United States Patent [19]
Fox

[11] Patent Number: 5,704,906
[45] Date of Patent: Jan. 6, 1998

[54] METHOD OF USING A TOPICAL ANESTHETIC-CLEANING SOLUTION AND APPLICATOR

[76] Inventor: Richard L. Fox, 9 Cranbury Ct., Edison, N.J. 08820

[21] Appl. No.: 606,902

[22] Filed: Feb. 26, 1996

[51] Int. Cl.[6] ................................................ A61M 35/00
[52] U.S. Cl. .......................................................... 604/1
[58] Field of Search .......................................... 604/1-3

[56] References Cited

U.S. PATENT DOCUMENTS

| | | | |
|---|---|---|---|
| 3,876,314 | 4/1975 | Nehring | 604/2 |
| 4,218,155 | 8/1980 | Weidner | 604/3 |
| 4,887,994 | 12/1989 | Bedford | 604/1 |
| 4,988,341 | 1/1991 | Columbus et al. | 604/304 |
| 5,112,297 | 5/1992 | Stalcup et al. | 604/1 |
| 5,120,325 | 6/1992 | Dow, Jr. | 604/304 |
| 5,295,952 | 3/1994 | Pietrafitta | 604/1 |
| 5,300,018 | 4/1994 | Walsh et al. | 604/1 |
| 5,358,480 | 10/1994 | Melcher et al. | 604/1 |
| 5,378,226 | 1/1995 | Hanifl | 604/3 |
| 5,384,048 | 1/1995 | Hazen et al. | 210/605 |
| 5,385,677 | 1/1995 | Venable | 210/748 |
| 5,433,950 | 7/1995 | Popp | 424/400 |
| 5,447,930 | 9/1995 | Nayak | 514/239.2 |

OTHER PUBLICATIONS

Packaging for Betadine Solution Swabstick (1993).

*Primary Examiner*—John G. Weiss
*Assistant Examiner*—Dennis Ruhl
*Attorney, Agent, or Firm*—Kenyon & Kenyon

[57] ABSTRACT

A topical anesthetic-cleansing solution and applicator are provided. The anesthetic-cleansing solution comprises an anesthetic agent such as Benzocaine and a cleansing solution such as alcohol. The applicator includes a swab and outer packaging housing the swab in a generally sterile environment. The swab includes an elongated member and an absorbent tip attached to the elongated member. The absorbent tip is impregnated with the anesthetic-cleansing solution. A method is also provided for using the applicator. The method includes the steps of holding a portion of the packaging covering the swab elongated member; removing a portion of the packaging covering the absorbent tip to expose the absorbent tip; and applying the absorbent tip on the patient's skin area to be anesthetized and cleansed.

2 Claims, 1 Drawing Sheet

METHOD OF USING A TOPICAL ANESTHETIC-CLEANING SOLUTION AND APPLICATOR

TECHNICAL FIELD OF THE INVENTION

The present invention relates generally to medical products and, more particularly, to topical anesthetic and cleansing solutions and applicators therefor.

BACKGROUND OF THE INVENTION

Cleansing solutions such as alcohol are normally applied to a patient's skin area where certain medical procedures are to be performed such as circumcision or insertion of a hypodermic needle for various purposes including administration of medications, blood withdrawal, and initiation of intravenous therapy. However, the skin area is often not anesthetized to reduce pain from the procedure since known means for applying anesthetic agents are cumbersome and time consuming.

An object of the present invention is to provide an anesthetic-cleansing solution that can be used to both cleanse and anesthetize the patient's skin.

A further object of the invention is to provide an applicator that can be used quickly and easily for applying the anesthetic-cleansing solution to the patient's skin. A further object of the invention is to provide an applicator that reduces the risk of contamination of the anesthetic-cleansing solution used.

SUMMARY OF THE INVENTION

A topical anesthetic-cleansing solution is provided in accordance with the invention. The anesthetic-cleansing solution comprises an anesthetic agent such as Benzocaine and a cleansing solution such as alcohol. Also, in accordance with the invention, an applicator is provided for the anesthetic-cleansing solution. The applicator includes a swab and outer packaging housing the swab in a generally sterile environment. The swab includes an elongated member and an absorbent tip attached to the elongated member. The absorbent tip is impregnated with the anesthetic-cleansing solution.

A method is also provided for using the applicator. The method includes the steps of holding a portion of the packaging covering the elongated member of the swab; removing a portion of the packaging covering the absorbent tip to expose the absorbent tip; and applying the absorbent tip on the patient's skin area to be anesthetized and cleansed.

The applicator can thus be used quickly and easily to anesthetize and cleanse a portion of a patient's skin. Since the applicator is maintained in a generally sterile environment until the time of use, the risk of contamination of the anesthetic-cleansing solution used is greatly reduced.

DETAILED DESCRIPTION

In accordance with the present invention, a topical anesthetic-cleansing solution is provided comprising an anesthetic agent such as Benzocaine and a sterile cleansing solution such as alcohol. The topical anesthetic-cleansing solution can be applied to the skin area where a procedure is to be performed such as, for example, insertion of a hypodermic needle to initiate intravenous therapy or circumcision. The anesthetic-cleansing solution both cleanses the skin area to reduce the risk of infection and temporarily deadens sensation to reduce pain during the procedure.

Figure 1:
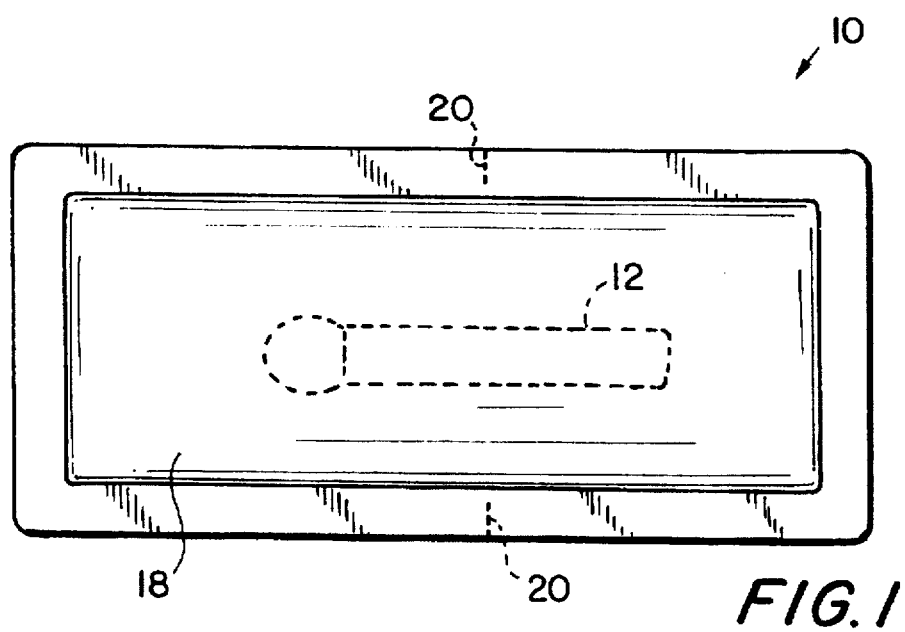
FIG. 1 is a top view of a topical anesthetic-cleansing solution applicator unit in accordance with the present invention.
Figure 2:
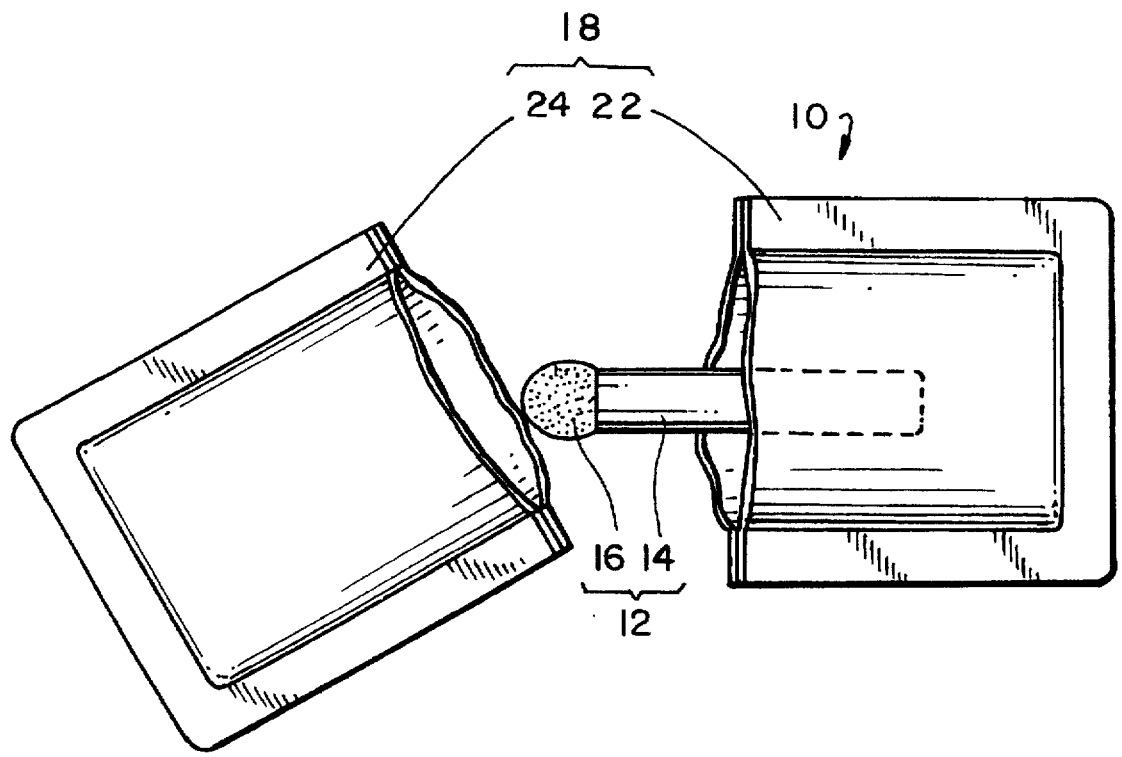
FIG. 2 is a top view of the FIG. 1 applicator unit shown with a portion of the applicator packaging removed and in condition for use.

The topical anesthetic-cleansing solution is maintained in sterile packaging such as the applicator unit 10 shown in FIGS. 1 and 2. The applicator 10 includes a swab 12, which comprises an elongated rod or member 14 and an absorbent applicator tip or element 16 attached to one end of the rod 14. The absorbent tip 16 is impregnated with the anesthetic-cleansing solution. The swab 12 is maintained in a generally sterile environment by outer packaging 18.

The swab applicator tip 16 may comprise a variety of absorbent or fluid retaining materials suitable for medical use such as, for example, cotton.

The outer packaging 18 may comprise a variety of materials, including paper and plastic materials, suitable for providing a generally sterile environment for the packaging contents. The packaging 18 generally comprises two sheets of materials that are heat-sealed around their periphery to form a sealed enclosed space therebetween. To facilitate opening of the package 18, portions of the heat-sealed areas of the package 18 may be weakened by, for example, being perforated as indicated by reference numeral 20.

To prepare the applicator 10 for use, the user holds the end of the package containing the swab rod (the first end) 22 with one hand, and tears off the opposite end of the package covering the absorbent tip (the second end) 24 with the other hand, thereby exposing the absorbent applicator tip 16. The second end 24 can be discarded. Then, while holding the first end 22 of the package, the exposed absorbent tip can be applied against the patient's skin area to be cleansed and anesthetized. By holding the outer package rather than the swab 12 directly, the user avoids exposing his or her own skin to the anesthetic agent. The applicator can be disposed after use.

Although not shown, other types of sterile packaging may also be used. Such packaging may include, for example, portions that can be peeled away to expose the absorbent tip of the swab.

Thus, the applicator 10 in accordance with the invention can be quickly and easily used to cleanse and anesthetize a portion of a patient's skin. Since the applicator 10 is maintained in a generally sterile environment up till the time of use, the risk of contamination of the anesthetic-cleansing solution used is substantially reduced.

The present invention has been described in the foregoing specification with respect to specific embodiments. These embodiments serve as examples to illustrate the invention rather than to limit its scope. Modifications may be made thereto without departing from the broader teachings of the invention.

I claim:

1. A method of applying a topical anesthetic-cleansing solution agent to a patient's skin area, comprising the steps of:

(a) providing an anesthetic-cleansing solution applicator comprising a swab including a member and an absorbent tip attached to said member, said absorbent tip being impregnated with a solution comprising a topical anesthetic agent and a cleansing solution; and said applicator also including outer packaging housing said swab in a generally sterile environment;

(b) holding a portion of the packaging covering the swab member;

(c) removing a portion of the packaging covering the absorbent tip to expose the absorbent tip; and (d) applying the absorbent tip on a portion of the patient's skin to be anesthetized and cleansed while holding the portion of the packaging covering the swab member.

2. The method of claim 1, wherein said packaging is at least partially perforated and step (c) comprises tearing off said portion of the packaging covering said absorbent tip.

* * * * *